(12) United States Patent
Therup et al.

(10) Patent No.: US 7,833,479 B2
(45) Date of Patent: Nov. 16, 2010

(54) CUVETTE AND A METHOD AND SHAPING TOOL FOR MANUFACTURE THEREOF

(75) Inventors: Ingrid Maria Therup, Ängelholm (SE); Norbert Pogorzelski, Helsingborg (SE); Bertil Johnny Ingemar Svensson, Ängelholm (SE); Per Goran Nilsson, Ängelholm (SE); Jan Anders Lennart Malm, Ängelholm (SE)

(73) Assignee: HemoCue AB, Angelholm (SE)

( * ) Notice: Subject to any disclaimer, the term of this patent is extended or adjusted under 35 U.S.C. 154(b) by 397 days.

(21) Appl. No.: 11/920,116

(22) PCT Filed: Jun. 28, 2006

(86) PCT No.: PCT/SE2006/000788
§ 371 (c)(1),
(2), (4) Date: Nov. 9, 2007

(87) PCT Pub. No.: WO2007/008137
PCT Pub. Date: Jan. 18, 2007

(65) Prior Publication Data
US 2009/0074620 A1 Mar. 19, 2009

(30) Foreign Application Priority Data
Jul. 8, 2005 (SE) .................................. 0501600

(51) Int. Cl.
*B01J 19/00* (2006.01)
(52) U.S. Cl. ........................ 422/72; 422/68.1; 422/99; 422/100; 422/102; 436/43; 436/165; 204/403.01; 204/451
(58) Field of Classification Search ............... 422/68.1, 422/100, 102; 436/43, 165; 204/403.01, 204/451; 356/246
See application file for complete search history.

(56) References Cited

U.S. PATENT DOCUMENTS 4,088,448 A  5/1978  Lilja et al.

(Continued)

FOREIGN PATENT DOCUMENTS

EP  0791394 A2  8/1997
WO  WO 9013016 A1  11/1990

OTHER PUBLICATIONS

International Search Report issued in conjunction with counterpart Swedish Application No. PCT/SE2006/000788 dated Oct. 10, 2006.
International Preliminary Report on Patentability issued in conjunction with counterpart Swedish Application No. PCT/SE2006/000788 dated Jun. 18, 2007.

*Primary Examiner*—Jill Warden
*Assistant Examiner*—Sharon Pregler
(74) *Attorney, Agent, or Firm*—Buchanan Ingersoll & Rooney PC

(57) ABSTRACT

A cuvette for taking up a body fluid sample and for providing the body fluid sample to an analysis comprises an inlet cavity for receiving a body fluid sample to be analyzed, a centrifugation reception cavity, which is arranged in communication with the inlet cavity such that spontaneous flow from the inlet cavity to the centrifugation reception cavity is prevented and such that body fluid from the inlet cavity may be forced into the centrifugation reception cavity by applying a centrifugation force on the cuvette, an analysis sample reception cavity, which is arranged in capillary connection with at least part of the centrifugation reception cavity for providing a sample transport by capillary action from the centrifugation reception cavity to the analysis sample reception cavity, wherein the analysis sample reception cavity has an opening through an outer wall of the cuvette, said opening extending over the entire width of the analysis sample reception cavity.

9 Claims, 3 Drawing Sheets

U.S. PATENT DOCUMENTS

| | | | |
|---|---|---|---|
| 4,387,992 A * | 6/1983 | Swartz | 356/246 |
| 5,286,454 A * | 2/1994 | Nilsson et al. | 422/102 |
| 5,472,671 A * | 12/1995 | Nilsson et al. | 422/102 |
| 5,674,457 A | 10/1997 | Williamsson et al. | |
| 6,468,807 B1 | 10/2002 | Svensson et al. | |
| 6,607,701 B1 | 8/2003 | Jansson et al. | |
| 2003/0164386 A1 * | 9/2003 | Connelly et al. | 222/361 |

* cited by examiner

CUVETTE AND A METHOD AND SHAPING TOOL FOR MANUFACTURE THEREOF

TECHNICAL FIELD

The present invention relates to a cuvette for taking up a body fluid sample and for providing the body fluid sample to an analysis. The present invention also relates to a method of manufacturing such a cuvette and a shaping tool for forming such a cuvette.

BACKGROUND OF THE INVENTION

A cuvette used for direct optical analysis of a fluid mixture is disclosed in U.S. Pat. No. 4,088,448. This cuvette comprises a body member including two planar surfaces spaced a predetermined distance from one another to determine an optical path and to define a cavity. The cavity has an inlet through which it communicates with the exterior of the body member. The cavity has a predetermined fixed volume, and the predetermined distance between the surfaces enables the cavity to take up a sample by capillary action. Further, a reagent is applied to the surfaces of the cavity.

U.S. Pat. No. 5,472,671 discloses a cuvette having several cavities. The cavities may be arranged such that fluid flow between the cavities may be controlled by centrifugation and allowing capillary transport. The several cavities enables a sample of whole blood to be introduced and analysis to be performed on plasma. Thus, the cuvette can be used for analysis within a much broader range than the cuvette according to U.S. Pat. No. 4,088,448. Further, the use of the centrifugal force for transport of fluid between cavities makes it possible to carry out different reactions in different cavities, thus allowing a period of incubation before the next reagent is used.

In U.S. Pat. No. 6,607,701, a method of manufacturing cuvettes is disclosed. The method comprises providing a first and a second sheet, providing at least one depression having a predetermined depth in at least one of the sheets, joining the first sheet and the second sheet for obtaining a body member with cavities, and cutting out micro-cuvettes from the body member. The method enables manufacture of a cuvette, wherein a deeper cavity is provided more remote from the sample inlet than a more shallow, capillary inlet cavity. This method will thus enable manufacture of complex designs of cavities within a cuvette.

SUMMARY OF THE INVENTION

It is an object of the invention to provide a cuvette that enables good control of separating a sample and mixing the sample with a reagent. It is a further object of the invention to provide a cuvette being designed so as to enable a reliable and simple manufacture of the cuvette.

These and other objects of the invention are accomplished by a cuvette, a method of manufacturing a cuvette, and a shaping tool according to the independent claims.

Thus, a cuvette is provided for taking up a body fluid sample and for providing the body fluid sample to an analysis. The cuvette comprises an inlet cavity for receiving a body fluid sample to be analysed, and a centrifugation reception cavity. The centrifugation reception cavity is arranged in communication with the inlet cavity such that spontaneous flow from the inlet cavity to the centrifugation reception cavity is prevented and such that body fluid from the inlet cavity may be forced into the centrifugation reception cavity by applying a centrifugation force on the cuvette. The cuvette further comprises an analysis sample reception cavity, which is arranged in capillary connection with at least part of the centrifugation reception cavity for providing a sample transport by capillary action from the centrifugation reception cavity to the analysis sample reception cavity. The analysis sample reception cavity has an opening through an outer wall of the cuvette, which opening extends over the entire width of the analysis sample reception cavity.

The cuvette is designed to be easily manufactured. The analysis sample reception cavity is placed in the cuvette such that it has an opening through an outer wall of the cuvette extending over the entire width of the analysis sample reception cavity. This implies that a shaping tool may be introduced into the cuvette for forming the analysis sample reception cavity and may be withdrawn from the cuvette without affecting other cavities of the cuvette. Thus, the analysis sample reception cavity may be formed by e.g. injection-moulding providing a cheap and simple manufacture of the cuvette. The arrangement of the analysis sample reception cavity such that it has an opening through an outer wall of the cuvette implies that the cuvette may be designed to allow transport of fluid through cavities of the cuvette in several, separate steps, while the cuvette may still be easily manufactured by the use of a shaping tool that may be withdrawn from the analysis sample reception cavity. The cuvette may therefore have a complex design of the cavities while enabling a simple manufacture of the cuvette.

The arrangement of cavities of the cuvette providing transport of fluid in several steps also enables the cuvette to provide reactions with the fluid in several steps. Thus, several different reagents may be provided in the cuvette, enabling more complex analyses to be performed in the cuvette.

The analysis sample reception cavity may be arranged to prevent spontaneous further transport of the sample from the cavity and thereby providing a defined sample volume.

The arrangement of the analysis sample reception cavity in capillary connection with at least part of the centrifugation reception cavity implies that a measurement may be performed on plasma or serum even when a sample of whole blood is acquired into the inlet cavity. The sample of whole blood is forced into the centrifugation reception cavity by applying a centrifugation force on the cuvette. The centrifugation force will separate red blood cells and plasma by the heavier red blood cells being pressed to the bottom of the centrifugation reception cavity. Then, the plasma may be drawn into the analysis sample reception cavity by means of capillary action. The analysis sample reception cavity preventing spontaneous further transport from the cavity implies that the analysis sample reception cavity defines a volume of plasma being drawn into the cavity. This well-defined sample volume may then be forced to further cavities in the cuvette or be analysed in the analysis sample reception cavity itself.

The cuvette may be arranged for acquiring e.g. a sample of whole blood, plasma, serum or urine. The sample introduced into the inlet cavity may be separated in the centrifugation reception cavity. For example, red blood cells may be separated out from a sample of whole blood or disturbing elements may be separated out from a sample of urine.

The inlet cavity may have an opening through an outer wall of the cuvette, which opening extends over the entire width of the inlet cavity. Since spontaneous transport of fluid from the inlet cavity is prevented, the opening of the inlet cavity makes it possible to acquire a sample into the inlet cavity in several steps. The opening extending over the entire width of the inlet cavity enables air bubbles in the inlet cavity to escape when the inlet cavity is filled in a second or subsequent step. The prevention of transport of fluid from the inlet cavity makes sure that the correct sample volume is acquired. Thus, if it is noted that the inlet cavity is not completely filled, the cuvette may again be brought in contact with a fluid to be sampled such that more fluid will be drawn into the inlet cavity by capillary action.

The cuvette may further comprise a measurement cavity, which is arranged in communication with the analysis sample reception cavity such that body fluid from the analysis sample reception cavity may be forced into the measurement cavity by applying a centrifugation force on the cuvette. The arrangement of the measurement cavity in communication with the analysis sample reception cavity implies that the sample being drawn up from the centrifugation reception cavity may be transported further. Thereby, the sample in the analysis sample reception cavity may be completely separated from the residue in the centrifugation reception cavity such that no fluid contact is maintained.

The analysis sample reception cavity may be arranged to slope towards the measurement cavity. This implies that fluid in the analysis sample reception cavity is directed towards the measurement cavity such that a small centrifugation force is able to force the fluid from the analysis sample reception cavity into the measurement cavity. The possibility of transporting fluid from the analysis sample reception cavity to the measurement cavity by means of applying only a small centrifugation force also implies that the risk of fluid being forced back into the centrifugation reception cavity during such centrifugation is diminished.

The cuvette may comprise an edge adapted to separate fluid in the analysis reception cavity from fluid in the centrifugation reception cavity, whereby the cuvette may be arranged to prevent siphon conduct of fluid from the centrifugation reception cavity to the measurement cavity. Thus, the residue in the centrifugation reception cavity is prevented from being mixed with the sample in the measurement cavity. The prevention of siphon conduct implies that there will be no exchange of fluid between the centrifugation reception cavity and the measurement cavity. Thus, the separation of fluids may be maintained in the measurement cavity.

The slope of the analysis sample reception cavity and the prevention of siphon conduct from the centrifugation reception cavity to the measurement cavity cooperate to ensure that a well-defined volume and content of the sample is maintained in the measurement cavity.

A channel between the analysis sample reception cavity and the measurement cavity may comprise an elbow. The elbow will prevent fluid from the measurement cavity to rise back into the analysis sample reception cavity even if an agitation force is applied to the cuvette for mixing the fluid in the measurement cavity with a reagent.

A reagent may be arranged in the measurement cavity. Thus, the sample that is transported into the measurement cavity may be mixed with a reagent in the measurement cavity. This implies that there is no need for preparing the sample before it is acquired by the cuvette. Thus, a measurement may be accomplished very easily using the cuvette.

The analysis sample reception cavity may be delimited by a thickness adjacent the cavity preventing capillary transport of fluid from the cavity. Capillary transport of fluids may occur through narrow vessels. By delimiting the analysis sample reception cavity with a relatively great thickness, capillary transport from the analysis sample reception cavity may be prevented.

A channel may provide the capillary communication between the analysis sample reception cavity and the centrifugation reception cavity and the channel may be arranged to end at a distance from the bottom of the centrifugation reception cavity. This is especially suitable where an analysis is to be performed on plasma and a sample of whole blood is acquired with the cuvette. The centrifugation will make the red blood cells accumulate at the bottom of the centrifugation reception cavity. Thus, the channel being arranged to end at a distance from the bottom implies that the capillary communication with the analysis sample reception cavity may draw plasma into the analysis sample reception cavity leaving the red blood cells at the bottom of the centrifugation reception cavity.

The analysis sample reception cavity may present a sharp edge at the interface with the channel. When the sample in the analysis sample reception cavity is forced into the measurement cavity, the sharp edge works to break fluid contact between the sample and the residue in the centrifugation reception cavity and the channel to the analysis sample reception cavity.

The invention also provides a method of manufacturing a cuvette for taking up a body fluid sample and for providing the body fluid sample to an analysis. The method comprises: providing a cuvette base material, from which the cuvette is to be formed, shaping a cuvette using at least one shaping tool. The shaping tool is arranged extending into said cuvette base material for forming a cuvette having: an inlet cavity for receiving a body fluid sample to be analysed, a centrifugation reception cavity, which is arranged in communication with the inlet cavity such that spontaneous flow from the inlet cavity to the centrifugation reception cavity is prevented and such that body fluid from the inlet cavity may be forced into the centrifugation reception cavity by applying a centrifugation force on the cuvette, and an analysis sample reception cavity, which is arranged in capillary connection with at least part of the centrifugation reception cavity for providing a sample transport by capillary action from the centrifugation reception cavity to the analysis sample reception cavity. The method further comprises withdrawing the shaping tool through a side wall of the cuvette.

This method comprises forming cavities of the cuvette by means of a shaping tool extending into a cuvette base material and withdrawing the shaping tool through a side wall of the cuvette. Thus, manufacture of the cuvette may be achieved in an automated process requiring few steps. The cavities may be simultaneously formed using the at least one shaping tool. Thus, a simple and cheap method of manufacturing a cuvette is provided.

The shaping of the cuvette may be performed by means of injection moulding, providing a simple and cheap method of manufacture suitable for using a shaping tool.

The shaping tool may be arranged extending into said cuvette base material for forming a cuvette that further comprises a measurement cavity, which is arranged in communication with the analysis sample reception cavity such that body fluid from the analysis sample reception cavity may be forced into the measurement cavity by applying a centrifugation force on the cuvette.

Thus, a cuvette is manufactured where a sample being drawn up from the centrifugation reception cavity may be transported further. Thereby, the sample in the analysis sample reception cavity may be completely separated from the residue in the centrifugation reception cavity such that no fluid contact is maintained. The measurement cavity may be formed using a shaping tool, whereby manufacture may still be simple and cheap.

The method may further comprise introducing a reagent into the measurement cavity and drying the reagent in the measurement cavity. Thus, the measurement cavity is provided with a reagent during manufacture, whereby there is no need to prepare a sample before it is acquired by the cuvette.

The invention further provides a shaping tool for forming a cuvette. The shaping tool is arranged for insertion into a cuvette base material for forming cavities in the base material and being further arranged to be withdrawn from the cuvette base material when the cavities have been formed. The shaping tool comprises: a first protrusion having an inverse shape of an inlet cavity of the cuvette, a second protrusion having an inverse shape of a centrifugation reception cavity of the cuvette, said second protrusion being arranged to form the centrifugation reception cavity adjacent the inlet cavity and said second protrusion having a thickness for preventing capillary transport of fluid from the inlet cavity to the centrifugation reception cavity, and a third protrusion having an inverse shape of an analysis sample reception cavity of the cuvette, said third protrusion being arranged to form the analysis sample reception cavity adjacent the centrifugation reception cavity and said third protrusion having a thickness allowing capillary transport of fluid from the centrifugation reception cavity to the analysis sample reception cavity.

This shaping tool enables a simple and cheap manufacturing method of a cuvette as described above.

The shaping tool may further comprise a fourth protrusion having an inverse shape of a measurement cavity of the cuvette, said fourth protrusion being arranged to form the measurement cavity adjacent the analysis sample reception cavity and said fourth protrusion having a thickness for preventing capillary transport of fluid from the analysis sample reception cavity to the measurement cavity.

The first and second protrusions may be arranged on a common, first shaping core and the third protrusion may be arranged on a second shaping core. Thus, the shaping tool may be used for manufacturing cuvettes of slightly different designs by substituting one of the shaping cores.

Alternatively, all protrusions are arranged on a common shaping core. This implies that the controlling of the shaping tool is simple, since there is no need of accurately relating two different shaping cores to each other.

According to another aspect of the invention, there is provided a cuvette for taking up a body fluid sample and for providing the body fluid sample to an analysis. The cuvette comprises: an inlet cavity for receiving a body fluid sample to be analysed, a centrifugation reception cavity, which is arranged in communication with the inlet cavity such that spontaneous flow from the inlet cavity to the centrifugation reception cavity is prevented and such that body fluid from the inlet cavity may be forced into the centrifugation reception cavity by applying a centrifugation force on the cuvette, an analysis sample reception cavity, which is arranged in capillary connection with at least part of the centrifugation reception cavity for providing a sample transport by capillary action from the centrifugation reception cavity to the analysis sample reception cavity, wherein said analysis sample reception cavity is arranged to prevent spontaneous further transport of the sample from the cavity and thereby providing a defined sample volume, and a measurement cavity, which is arranged in communication with the analysis sample reception cavity such that body fluid from the analysis sample reception cavity may be forced into the measurement cavity by applying a centrifugation force on the cuvette.

The arrangement of the analysis sample reception cavity in capillary connection with at least part of the centrifugation reception cavity implies that a measurement may be performed on plasma or serum even when a sample of whole blood is acquired into the inlet cavity. The sample of whole blood is forced into the centrifugation reception cavity by applying a centrifugation force on the cuvette. The centrifugation force will separate red blood cells and plasma by the heavier red blood cells being pressed to the bottom of the centrifugation reception cavity. Then, the plasma may be drawn into the analysis sample reception cavity by means of capillary action. The analysis sample reception cavity preventing spontaneous further transport from the cavity implies that the analysis sample reception cavity defines a volume of plasma being drawn into the cavity. This well-defined sample volume may then be forced to further cavities in the cuvette or be analysed in the analysis sample reception cavity itself.

The cuvette provides a possibility to obtain a well-defined sample volume in the analysis sample reception cavity. The cuvette allows acquiring a sample of whole blood in the inlet cavity and presenting a sample of plasma in the analysis sample reception cavity. This implies that there is no need of separating plasma before acquiring a sample with the cuvette. This makes the cuvette very easy to use.

BRIEF DESCRIPTION OF THE DRAWINGS

The invention will now be described in further detail by way of example only with reference to the accompanying drawings.

DETAILED DESCRIPTION OF A PREFERRED EMBODIMENT

Figure 1A:
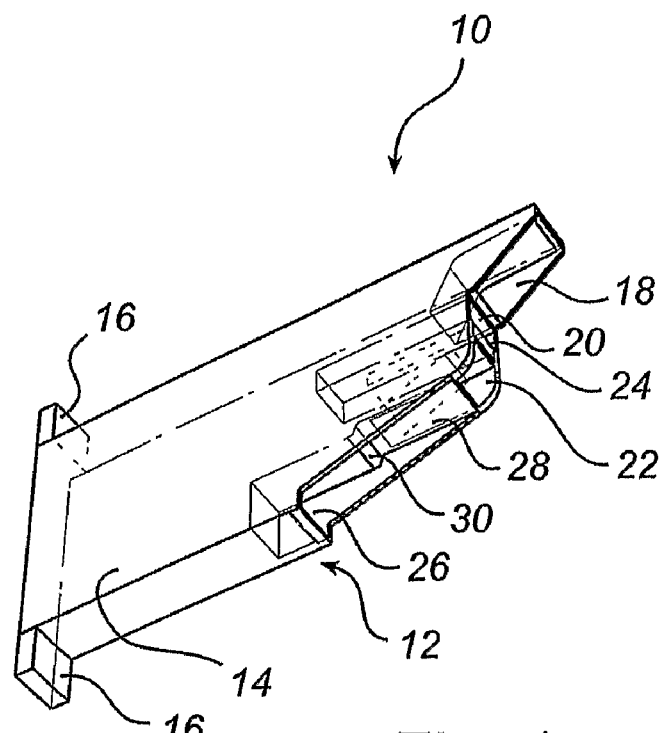
FIG. 1 is a perspective view of a cuvette according to a first embodiment of the present invention.
Figure 1B:
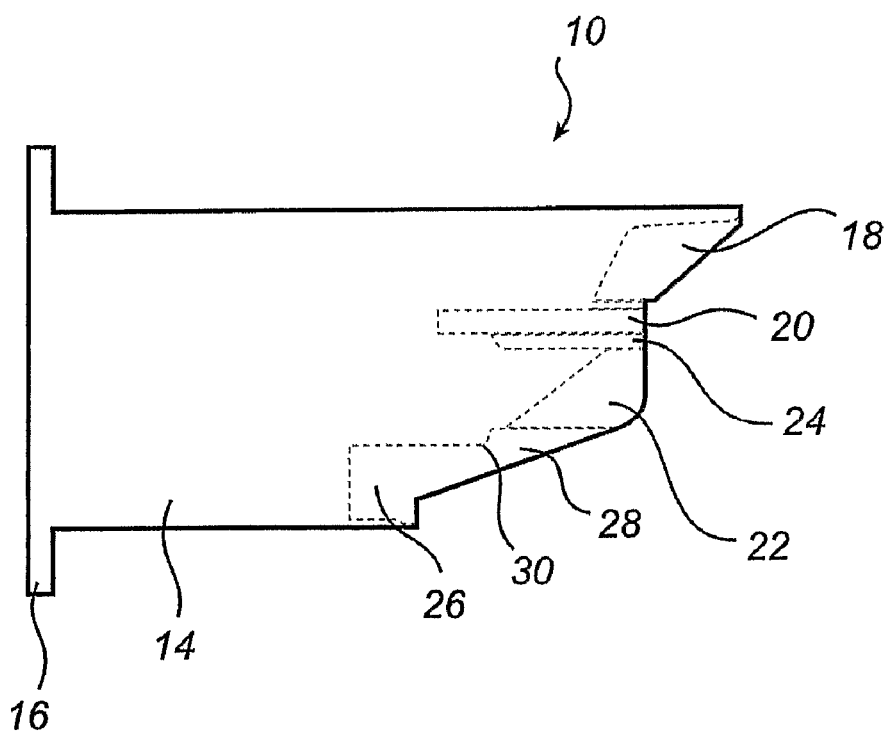

Referring now to FIG. 1, a cuvette 10 according to an embodiment of the invention will be described. The cuvette 10 is disposable and is to be thrown away after having been used for analysis. This implies that the cuvette 10 does not require complicated handling.

The cuvette 10 may be used for analysing a sample of any body fluid, such as whole blood, plasma, serum or urine. However, in the following description, reference will be made only to analysis of a sample of whole blood. A person skilled in the art would be able to implement analysis of other body fluids based on the description below.

The cuvette 10 comprises a body member 12, which has a base 14, which may be touched by an operator without causing any interference in analysis results. The base 14 may also have projections 16 that may fit a cuvette holder in an analysis apparatus. The projections 16 may be arranged such that the cuvette 10 will be correctly positioned in the analysis apparatus.

The cuvette 10 comprises cavities that are formed in the body member 12 and are defined by opposite walls within the body member 12. The cavities are open through an outer wall of the body member 12, such that the cavities may be formed during manufacture of the cuvette 10 by means of a shaping tool which is withdrawn from the cuvette 10 when the cavities have been formed. Each cavity has a width and a height, which are described by a non-decreasing function towards the outer wall of the cuvette. Thus, the shaping tool may be withdrawn without affecting the cavity that has been formed.

The cuvette 10 comprises an inlet cavity 18. The inlet cavity 18 is defined between opposite walls within the cuvette 10, the walls being arranged so close to each other that a capillary force may be created in the inlet cavity 18. The inlet cavity 18 communicates with the exterior of the cuvette 10 for allowing blood to be drawn into the cuvette 10. The inlet cavity 18 is arranged at a tip of the cuvette 10 to facilitate drawing up a sample into the inlet cavity 18.

The cuvette 10 further comprises a centrifugation reception cavity 20. The centrifugation reception cavity 20 has a thickness to prevent capillary transport of fluid from the inlet cavity 18. The inlet cavity 18 may have an area adjacent to the centrifugation reception cavity 20 that has a very narrow thickness to further ensure that there is no capillary transport from the inlet cavity 18 to the centrifugation reception cavity 20. The cuvette 10 may be exposed to an external centrifugation force in order to force fluid from the inlet cavity 18 into the centrifugation reception cavity 20.

Since the cuvette 10 is arranged such that transport from the inlet cavity 18 is prevented, the inlet cavity 18 may be filled with a sample in several steps without acquiring excess fluid. Thus, when the inlet cavity 18 has not been properly filled, more fluid may be drawn into the inlet cavity 18 for filling up the cavity. This implies that a well-defined sample volume corresponding to the volume of the inlet cavity 18 may always be acquired. Further, the inlet cavity 18 is open through an outer wall of the cuvette 10 such that air bubbles are able to escape for properly filling the inlet cavity 18.

The cuvette further comprises an analysis sample reception cavity 22, which is in fluid communication with the centrifugation reception cavity 20. There is a channel 24 connecting the analysis sample reception cavity 22 with the centrifugation reception cavity 20. The channel 24 ends at a distance from the bottom of the centrifugation reception cavity 20. The channel 24 and the analysis sample reception cavity 22 have walls arranged so close together that a capillary force may be created to draw fluid from the centrifugation reception cavity 20 into the analysis sample reception cavity 22. Since the channel 24 ends at a distance from the bottom of the centrifugation reception cavity 20, a residue of the sample will be left in the centrifugation reception cavity 20. This implies that the analysis sample reception cavity 22 may receive specific parts of the acquired sample which parts have been separated from the rest of the sample during centrifugation. The analysis sample reception cavity 22 may have a sharp edge towards the channel 24. The sharp edge provides a fluid splitting function such that fluid being transported from the analysis sample reception cavity 22 may be separated from the fluid in the channel 24.

The analysis sample reception cavity 22 has very narrow edges to prevent capillary transport away from the analysis sample reception cavity 22. This implies that the analysis sample reception cavity 22 will receive fluid filling the cavity 22 but no fluid may escape the cavity 22 without the cuvette 10 being exposed to an external force. Thus, a well-defined sample volume will be drawn into the analysis sample reception cavity 22.

The cuvette 10 further comprises a measurement cavity 26 and a channel 28 connecting the analysis sample reception cavity 22 with the measurement cavity 26. The channel 28 has a thickness to prevent capillary transport of fluid from the analysis sample reception cavity 22. The cuvette 10 may again be exposed to an external centrifugation force in order to force fluid from the analysis sample reception cavity 22 into the measurement cavity 26. The analysis sample reception cavity 22 slopes towards the measurement cavity 26. This implies that there is only needed a small centrifugation force for forcing the fluid from the analysis sample reception cavity 22 into the measurement cavity 26. During the further centrifugation, the sharp edge of the analysis sample reception cavity 22 will split the fluid in fluid being passed from the analysis sample reception cavity 22 into the measurement cavity 26 and fluid being pushed in the channel 24 back into the centrifugation reception cavity 20.

The measurement cavity 26 comprises a reagent. The sample received in the measurement cavity 26 is to react with the reagent before a measurement is performed on the sample. The reagent may be arranged on the surfaces of the walls of the measurement cavity 26 such that the sample will make contact with the reagent as soon as it enters the measurement cavity 26. Thus, the reaction is initiated as soon as the sample enters the measurement cavity 26.

Alternatively, the reagent may be arranged in a separate part of the measurement cavity 26 such that it is possible to make a blank measurement on the sample before the reaction has started. The reagent will dissolve and an external agitation force may be exerted on the cuvette 10 for thoroughly mixing the sample with the reagent.

The channel 28 comprises an elbow 30. This implies that fluid is prevented from rising back into the analysis sample reception cavity 22 during mixing of the sample with a reagent.

The cuvette 10 enables controlling the transport of fluid to different cavities. Exchange of fluid between the centrifugation reception cavity 20 and the measurement cavity 26 is prevented after the sample has been brought to the measurement cavity 26. The second centrifugation will separate fluid in the different cavities. Thus, the analysis sample reception cavity 22 may be completely dried up. Siphon conduct is then prevented, since there is no fluid contact between the fluid in the centrifugation reception channel 20 and the fluid in the measurement cavity 26.

Figure 2:
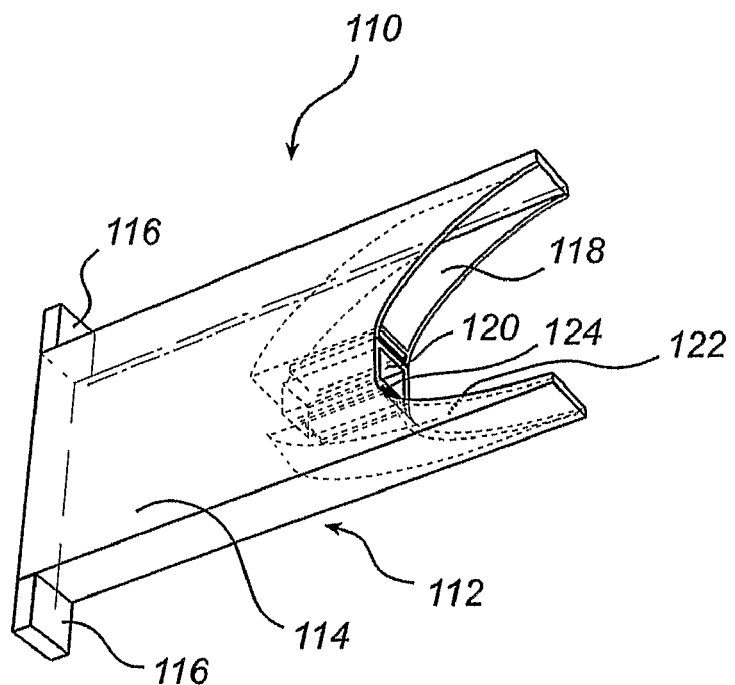
FIG. 2 is a perspective view of a cuvette according to a second embodiment of the present invention.

Referring now to FIG. 2, a cuvette 110 according to a second embodiment will be described. The cuvette 110 resembles the cuvette 10 of the first embodiment. However, the cuvette 110 does not comprise a measurement cavity. The cuvette 110 is arranged for performing an analysis on a sample in the analysis sample reception cavity 122. The reagent is arranged in the analysis sample reception cavity 122. This cuvette 110 may still be used for separating plasma from a sample of whole blood and, using a modest agitation force, the plasma may be mixed with the reagent in the analysis sample reception cavity 122 without introducing red blood cells into the analysis sample reception cavity 122.

According to alternative embodiments, the cavities of the cuvette are placed in different relationships to each other. According to one alternative, the measurement cavity and the channel between the analysis reception cavity and the measurement cavity need not be arranged to be open directly through an outer wall of the body member. Instead, these spaces may be arranged inside the analysis reception cavity and may still be formed by means of a shaping tool which is withdrawn from the cuvette when the cavities have been formed. The channel and the measurement cavity may be arranged having a smaller width and height than the analysis reception cavity and may thus be formed by a shaping tool that may be withdrawn without affecting the shape of the analysis reception cavity. According to another alternative, the analysis reception cavity may be arranged in direct connection to the centrifugation reception cavity for receiving fluid by capillary action from a part of the centrifugation reception cavity adjoining the analysis reception cavity. According to yet another alternative, the cavities may be formed to be open through two adjoining outer walls of the cuvette. Thus, different cavities may be formed by two different shaping tools that are to form the respective cavities extending from two adjoining walls in the cuvette. For example, a first shaping tool may form the inlet cavity and the centrifugation reception cavity extending from one wall of the cuvette. A second shaping tool may form the analysis reception cavity and the channel between the centrifugation reception cavity and the analysis reception cavity and the measurement cavity extending from an adjoining wall of the cuvette. The two shaping tools need to make contact in the cuvette for allowing the different cavities to be connected to each other.

A method of performing an analysis using the cuvette 10 will now be described. A sample of whole blood is drawn into the cuvette 10. The sample may be acquired directly from a pricked finger. Thus, the blood sample may be acquired very easily causing practically no pain to a patient. The cuvette 10 is then placed in an analysis instrument. The cuvette 10 is rotated by the analysis instrument such that the fluid in the inlet cavity 18 is forced into the centrifugation reception cavity 20 by the movement of the cuvette 10. The cuvette 10 is thereafter brought to a standstill while the sample is in the centrifugation reception cavity 20. The sample of whole blood has now been separated into red blood cells and plasma. The red blood cells, which are relatively heavy, are pressed to the bottom of the centrifugation reception cavity 20. Plasma is drawn into the analysis sample reception cavity 22 by means of a capillary force through the channel 24. Then, the cuvette 10 is again rotated such that the sample of plasma in the analysis sample reception cavity 22 is forced into the measurement cavity 26. The cuvette 10 is rotated with the analysis sample reception cavity 22 leading the measurement cavity 26 in the rotating movement. This implies that the fluid in the analysis sample reception cavity 22 is also somewhat pressed by the rotating movement towards the measurement cavity 26, which further ensures that the sample in the analysis sample reception cavity 22 is forced into the measurement cavity 26.

Figure 3:
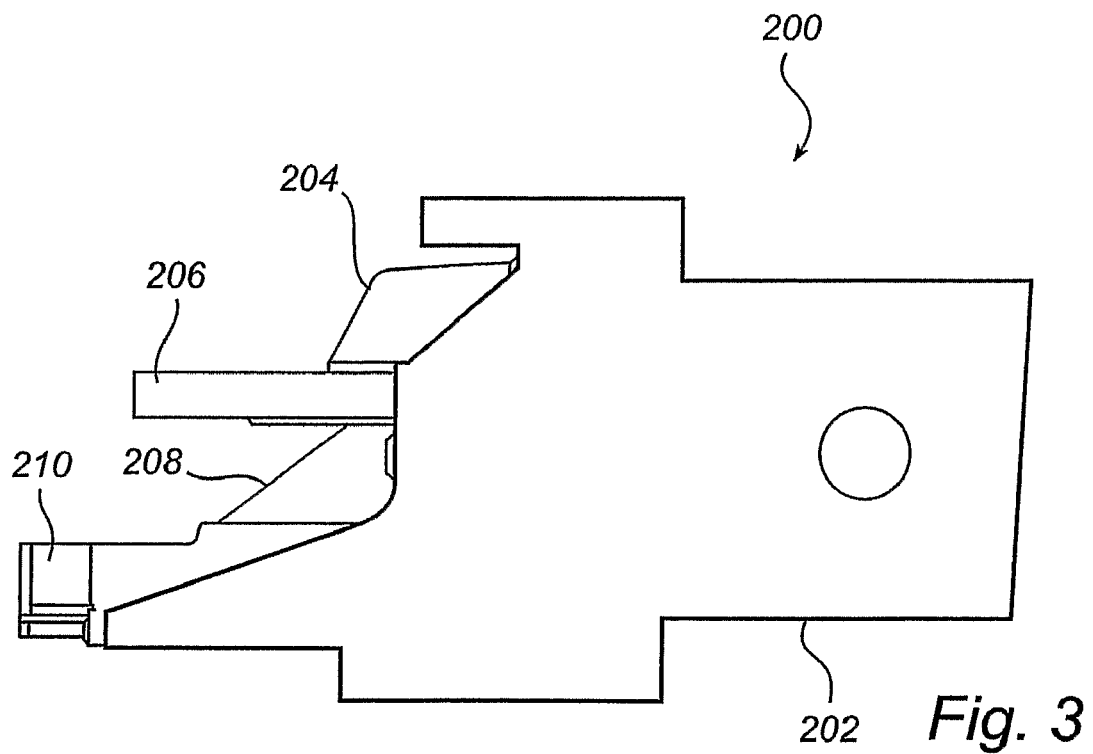
FIG. 3 is a perspective view of a shaping tool for manufacture of the cuvette of FIG. 1.

Referring now to FIG. 3, a shaping tool 200 for shaping a cuvette during manufacture will be described. The shaping tool 200 has a base 202, which provides a grip for being handled by a instrument during manufacture of the cuvette. The shaping tool 200 is to be introduced to extend into the cuvette for forming cavities during manufacture and withdrawn from the cuvette after the cavities have been formed. The shaping tool 200 has protrusions 204, 206, 208, 210 corresponding to the cavities to be formed. The protrusions 204, 206, 208, 210 have inverse shapes to the cavities. The protrusions 204, 206, 208, 210 are arranged side by side on the shaping tool 200 such that the cavities will be formed in connection to each other in the cuvette. The protrusions 204, 206, 208, 210 may be arranged on one common shaping core as shown in FIG. 3.

Alternatively, the shaping tool 200 may comprise two or more separate shaping cores that may provide one or more protrusions. The design of the cuvette being produced may be flexibly changed in the production line by simply replacing one or more shaping cores. Thus, the same shaping core may be used for several different designs of the cuvette.

The shaping tool 200 has a first protrusion 204 having an inverse shape of an inlet cavity of the cuvette, a second protrusion 206 having an inverse shape of a centrifugation reception cavity of the cuvette, a third protrusion 208 having an inverse shape of an analysis sample reception cavity of the cuvette, and a fourth protrusion 210 having an inverse shape of a measurement cavity of the cuvette.

Figure 4:
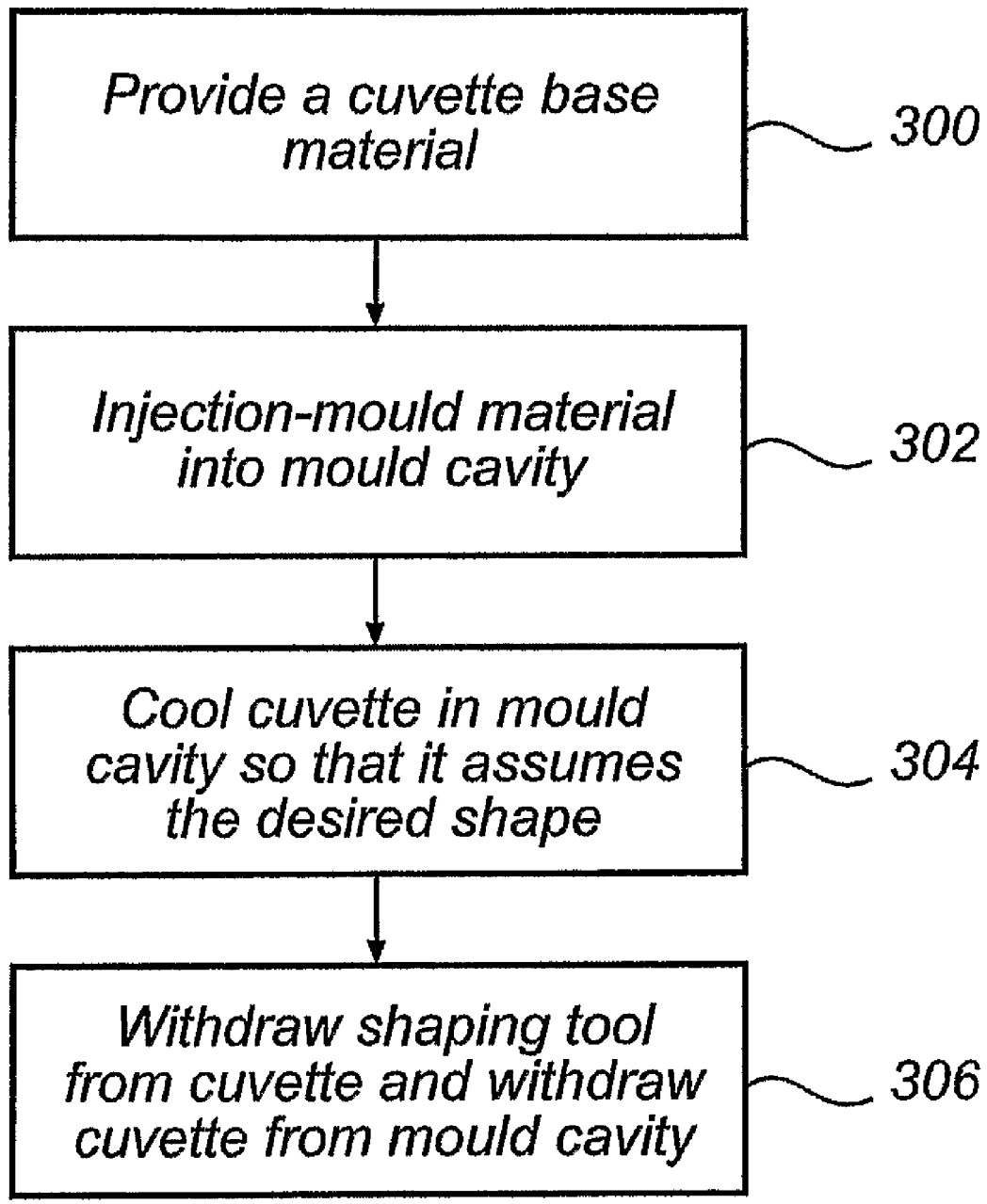
FIG. 4 is a flow chart of a method for manufacture of the cuvette.

Referring now to FIG. 4, a method for manufacture of a cuvette will be described. First, a cuvette base material is provided, step 300. This may be a plastic material having a low absorbance of radiation in the wavelengths to be used during the analysis. Such materials may be e.g. polystyrene, PMMA, or polycarbonate.

The cuvette base material is melted to create a moulding material and the moulding material is injection-moulded into a mould cavity, step 302. The shaping tool extends into the mould cavity so that cavities are formed in the cuvette. The cuvette is cooled in the mould cavity to assume the desired shape, step 304. When the shape has been stabilized, the shaping tool is withdrawn from the cuvette and the completed cuvette may be withdrawn from the mould cavity, step 306.

The manufacturing method is suitable for being completely automated. Cuvettes may be manufactured at a high rate. This makes the manufacturing method simple and cheap.

It should be emphasized that the preferred embodiments described herein are in no way limiting and that many alternative embodiments are possible within the scope of protection defined by the appended claims.

The invention claimed is:

1. A cuvette for taking up a body fluid sample and for providing the body fluid sample to an analysis, said cuvette comprising:
   an inlet cavity for receiving a body fluid sample to be analyzed,
   a centrifugation reception cavity, which is arranged in communication with the inlet cavity such that spontaneous flow from the inlet cavity to the centrifugation reception cavity is prevented and such that body fluid from the inlet cavity may be forced into the centrifugation reception cavity by applying a centrifugation force on the cuvette,
   an analysis sample reception cavity, which is arranged in capillary connection with at least part of the centrifugation reception cavity for providing a sample transport by capillary action from the centrifugation reception cavity to the analysis sample reception cavity,
   a measurement cavity, which is arranged in communication with the analysis sample reception cavity such that body fluid from the analysis sample reception cavity may be forced into the measurement cavity by applying a centrifugation force on the cuvette,
   wherein the inlet cavity, the centrifugation reception cavity, the analysis sample reception cavity and the measurement cavity have openings through an outer wall of the cuvette, said openings extending over the entire width of the cavities, respectively.

2. The cuvette according to claim 1, wherein said analysis sample reception cavity is arranged to prevent spontaneous further transport of the sample from the cavity and thereby providing a defined sample volume.

3. The cuvette according to claim 1, wherein the analysis sample reception cavity is arranged to slope towards the measurement cavity.

4. The cuvette according to claim 1, wherein the cuvette comprises a sharp edge adapted to separate fluid in the analysis reception cavity from fluid in the centrifugation reception cavity, whereby the sharp edge is arranged to break fluid contact between the sample and the residue in the centrifugation reception cavity and a channel to the analysis sample reception cavity and prevent siphon conduct of fluid from the centrifugation reception cavity to the measurement cavity.

5. The cuvette according to claim 1, wherein a channel between the analysis sample reception cavity and the measurement cavity comprises an elbow.

6. The cuvette according to claim 1, wherein a reagent is arranged in the measurement cavity.

7. The cuvette according to claim 1, wherein the analysis sample reception cavity is delimited by a thickness adjacent the cavity preventing capillary transport of fluid from the cavity.

8. The cuvette according to claim 4, wherein the channel provides the capillary communication between the analysis sample reception cavity and the centrifugation reception cavity, said channel being arranged to end at a distance from the bottom of the centrifugation reception cavity.

9. The cuvette according to claim 1, wherein the cuvette comprises a body member having inner walls defining said cavities within the body member.

* * * * *